United States Patent
Lobben

(10) Patent No.: US 7,504,521 B2
(45) Date of Patent: Mar. 17, 2009

(54) METHODS FOR THE PREPARATION OF PYRROLOTRIAZINE COMPOUNDS

(75) Inventor: Paul C. Lobben, Lawrenceville, NJ (US)

(73) Assignee: Bristol-Myers Squibb Co., Princeton, NJ (US)

( * ) Notice: Subject to any disclaimer, the term of this patent is extended or adjusted under 35 U.S.C. 154(b) by 301 days.

(21) Appl. No.: 11/197,970

(22) Filed: Aug. 5, 2005

(65) Prior Publication Data
US 2006/0030708 A1 Feb. 9, 2006

Related U.S. Application Data

(60) Provisional application No. 60/599,135, filed on Aug. 5, 2004.

(51) Int. Cl.
*C07D 207/30* (2006.01)
*C07D 487/04* (2006.01)

(52) U.S. Cl. ...................... 548/557; 548/561
(58) Field of Classification Search ................ 548/557, 548/561
See application file for complete search history.

(56) References Cited

U.S. PATENT DOCUMENTS

| | | | |
|---|---|---|---|
| 4,200,750 A | 4/1980 | Warner, Jr. et al. | |
| 4,908,056 A | 3/1990 | Tseng | |
| 5,658,903 A | 8/1997 | Adams et al. | |
| 5,686,457 A | 11/1997 | Traxler et al. | |
| 5,932,576 A | 8/1999 | Anantanarayan et al. | |
| 5,945,418 A | 8/1999 | Bemis et al. | |
| 5,977,103 A | 11/1999 | Adams et al. | |
| 6,087,496 A | 7/2000 | Anantanarayan et al. | |
| 6,130,235 A | 10/2000 | Mavunkel et al. | |
| 6,147,080 A | 11/2000 | Bemis et al. | |
| 6,251,914 B1 | 6/2001 | Adams et al. | |
| 6,277,989 B1 | 8/2001 | Chakravarty et al. | |
| 6,518,269 B1 | 2/2003 | Camden et al. | |
| 6,589,947 B1 | 7/2003 | Hamanaka et al. | |
| 6,670,357 B2 | 12/2003 | Leftheris et al. | |
| 6,867,300 B2 | 3/2005 | Godfrey, Jr. et al. | |
| 6,869,952 B2 | 3/2005 | Bhide et al. | |
| 6,900,217 B2 | 5/2005 | Chen | |
| 6,906,067 B2 | 6/2005 | Moriarty et al. | |
| 6,908,916 B2 | 6/2005 | Mastalerz et al. | |
| 6,916,815 B2 | 7/2005 | Vite et al. | |
| 6,933,386 B2 | 8/2005 | Bhide et al. | |
| 6,951,859 B2 | 10/2005 | Bhide et al. | |
| 6,962,915 B2 | 11/2005 | Das et al. | |
| 6,969,717 B2 | 11/2005 | Bhide et al. | |
| 6,982,265 B1 | 1/2006 | Hunt et al. | |

(Continued)

FOREIGN PATENT DOCUMENTS

| EP | 0 713 876 | 5/1996 |
|---|---|---|
| EP | 0 795 556 | 9/1997 |
| EP | 0 778 277 | 6/2003 |
| WO | WO 98/08847 | 3/1998 |
| WO | WO 99/24033 | 5/1999 |
| WO | WO 00/12074 | 3/2000 |
| WO | WO 00/12497 | 3/2000 |
| WO | WO 00/20402 | 4/2000 |
| WO | WO 00/56738 | 9/2000 |
| WO | WO 00/71129 | 11/2000 |
| WO | WO 01/14378 | 3/2001 |
| WO | WO 01/27089 | 4/2001 |
| WO | WO 01/34605 | 5/2001 |

(Continued)

OTHER PUBLICATIONS

Chemical Abstract, vol. 88, No. 121113q, p. 541 (1978).

(Continued)

*Primary Examiner*—Venkataraman Balasubramanian
(74) *Attorney, Agent, or Firm*—Laurelee A. Duncan

(57) ABSTRACT

A method for preparing a compound having the formula:

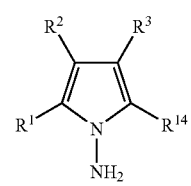

III including the steps of:
(a) cyclizing a compound of formula II:

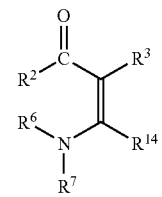

II to form a compound of formula I:

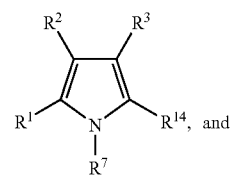

I (b) deprotecting the nitrogen atom of the compound of formula I by amination or hydrogenation to form compound III.

9 Claims, No Drawings

U.S. PATENT DOCUMENTS

| | | | |
|---|---|---|---|
| 2001/0041673 A1 | 11/2001 | Fossa |
| 2002/0065270 A1 | 5/2002 | Moriarty et al. |
| 2003/0139435 A1 | 7/2003 | Ahmed et al. |
| 2003/0232831 A1 | 12/2003 | Dyckman et al. |
| 2003/0232832 A1 | 12/2003 | Lombardo et al. |
| 2004/0082582 A1 | 4/2004 | Dyckman et al. |
| 2004/0157846 A1 | 8/2004 | Chen et al. |
| 2004/0229877 A1 | 11/2004 | Leftheris et al. |
| 2005/0043306 A1 | 2/2005 | Leftheris et al. |
| 2005/0124621 A1 | 6/2005 | Bhide et al. |
| 2005/0143398 A1 | 6/2005 | Das et al. |
| 2005/0182058 A1 | 8/2005 | Fink et al. |
| 2005/0197339 A1 | 9/2005 | Gavai et al. |
| 2005/0209454 A1 | 9/2005 | Swaminathan et al. |
| 2005/0245530 A1 | 11/2005 | Borzilleri et al. |
| 2006/0003967 A1 | 1/2006 | Shi et al. |
| 2006/0004006 A1 | 1/2006 | Borzilleri et al. |
| 2006/0009454 A1 | 1/2006 | Cai et al. |
| 2006/0014745 A1 | 1/2006 | Gavai et al. |
| 2006/0019928 A1 | 1/2006 | Lin et al. |

FOREIGN PATENT DOCUMENTS

| | | |
|---|---|---|
| WO | WO 01/47897 | 7/2001 |
| WO | WO 02/40486 | 5/2002 |
| WO | WO 03/002542 | 1/2003 |
| WO | WO 03/002544 | 1/2003 |
| WO | WO 03/042172 | 5/2003 |
| WO | WO 03/090912 | 11/2003 |
| WO | WO 03/091229 | 11/2003 |
| WO | WO 03/099286 | 12/2003 |
| WO | WO 2004/009542 | 1/2004 |
| WO | WO 2004/009601 | 1/2004 |
| WO | WO 2004/009784 | 1/2004 |
| WO | WO 2004/013145 | 2/2004 |
| WO | WO 2004/043912 | 5/2004 |
| WO | WO 2004/054514 | 7/2004 |
| WO | WO 2004/072030 | 8/2004 |
| WO | WO 2005/042537 | 5/2005 |
| WO | WO 2005/058245 | 6/2005 |
| WO | WO 2005/065266 | 7/2005 |
| WO | WO 2005/066176 | 7/2005 |

OTHER PUBLICATIONS

Connolly, D.T. et al., "Human Vascular Permeability Factor", The Journal of Biological Chemistry, vol. 264, No. 33, pp. 20017-20024 (1989).

Cullinan-Bove, K. et al., "Vascular Endothelial Growth Factor/Vascular Permeability Factor Expression in the Rat Uterus: Rapid Stimulation by Estrogen-Induced Increases in Uterine Capillary Permeability and Growth", Endocrinology, vol. 133, No. 2, pp. 829-837 (1993).

de Vries, C. et al., "The fms-Like Tyrosine Kinase, a Receptor for Vascular Endothelial Growth Factor", Science, vol. 255, pp. 989-991 (1992).

Eskins, F., "Angiogenesis inhibitors in clinical development; where are we now and where are we going?", British Journal of Cancer, vol. 90, No. 1, pp. 1-7 (2004).

Ewald, H. et al., "Reactions of 1,2,4-Triazines with Dimethyl Acetylenedicarboxylate", Liebigs Ann. Chem., pp. 1718-1724 (1977).

Fabbro, D. et al., "Protein kinases as targets for anticancer agents: from inhibitors to useful drugs", Pharmacology & Therapeutics, vol. 93, pp. 79-98 (2002).

Fan, T.-P.D. et al., "Controlling the vasculature: angiogenesis, antiangiogenesis and vascular targeting of gene therapy", Trends in Pharmacological Sciences, vol. 16, pp. 57-66 (1995).

Folkman, J., "Angiogenesis in cancer, vascular rheumatoid and other disease", Nature Medicine, vol. 1, No. 1, pp. 27-31 (1995).

Haque, S.A. et al., "Monastrol, a Prototype Anti-Cancer Drug That Inhibits a Mitotic Kinesin, Induces Rapid Bursts of Axonal Outgrowth From Cultured Postmitotic Neurons", Cell Motility and the Cytoskeleton, vol. 58, No. 10-16 (2004).

Henry, J.R. et al., "p38 mitogen-activated protein kinase as a target for drug discovery", Drugs of the Future, vol. 24, No. 12, pp. 1345-1354 (1999).

Jaffari, G.A. et al., "Some Oxidation Reactions of Monochloramine", J. Chem. Soc. (C), pp. 823-826 (1971).

Jakeman, L.B. et al., "Developmental Expression of Binding Sites and Messenger Ribonucleic Acid for Vascular Endothelial Growth Factor Suggests a Role for This Protein in Vasculogenesis and Angiogenesis", Endocrinology, vol. 133, No. 2, pp. 848-859 (1993).

Kapoor, T.M. et al., "Probing Spindle Assembly Mechanisms with Monastrol, a Small Molecule Inhibitor of the Mitotic Kinesin, Eg5", The Journal of Cell Biology, vol. 150, No. 5, pp. 975-988 (2000).

Kolch, W. et al., "Regulation of the expression of the VEGF/VPS and its receptors: role in tumor angiogenesis", Breast Cancer Research and Treatment, vol. 36, pp. 139-155 (1995).

Mayer, T.U. et al., "Small Molecule Inhibitor of Mitotic Spindle Bipolarity Identified in a Phenotype-Based Screen", Science, vol. 286, pp. 971-974 (1999).

Migliara, O. et al., "Synthesis of a New Bridgehead Nitrogen Heterocyclic System. Pyrrolo[2,1-f]-1,2,4-triazine Derivatives", J. Heterocyclic Chem., vol. 16, pp. 833-834 (1979).

Moreland, L.W. et al., "Etanercept Therapy in Rheumatoid Arthritis: A Randomized, Controlled Trial", Ann. Intern. Med., vol. 130, No. 6, pp. 478-486 (1999).

Neunhoeffer, H. et al., "Cycloaddition Reactions with Methoxy- and Dialkylamino-1,2,4-triazines", Liebigs Ann. Chem., pp. 1413-1420 (1977).

Otter, B.A. et al., "Conformational Properties of Purine-Like C-Nucleosides", Nucleosides & Nucleotides, vol. 15, Nos. 1-3, pp. 793-807 (1996).

Patil, S.A. et al., "Synthesis of Pyrrolo[2,1-f][1,2,4]triazine Congeners of Nucleic Acid Purines via the N-Amination of 2-Substituted Pyrroles", J. Heterocyclic Chem., vol. 31, pp. 781-786 (1994).

Quintela, J.M. et al., "A Ready One-pot Preparation for Pyrrolo[2,1-f][1,2,4]triazine and Pyrazolo[5,1-c]pyrimido[4,5-e][1,2,4]triazine Derivatives", Tetrahedron, vol. 52, No. 8, pp. 3037-3048 (1996).

Raingeaud, J. et al., "MKK3- and MKK6-Regulated Gene Expression Is Mediated by the p38 Mitogen-Activated Protein Kinase Signal Transduction Pathway", Molecular and Cellular Biology, vol. 16, No. 3, pp. 1247-1255 (1996).

Rankin, E.C.C. et al., "The Therapeutic Effects of an Engineered Human Anti-Tumor Necrosis Factor Alpha Antibody (CDP571) in Rheumatoid Arthritis", British Journal of Rheumatology, vol. 34, pp. 334-342 (1995).

Salituro, F.G. et al., "Inhibitors of p38 MAP Kinase: Therapeutic Intervention in Cytokine-Mediated Diseases", Current Medicinal Chemistry, vol. 6, No. 9, pp. 807-823 (1999).

Selič, L. et al., "Transformations of Alkyl 2-(2,2-Disubstituted-ethenyl)amino-3-dimethylaminoprop-2-enoates: Synthesis of Alkyl 3,4-Disubstituted- and Alkyl 1-Acyl-3,4-disubstituted Pyrrole-2-carboxylates", Synthesis, No. 3, pp. 479-482 (1999).

Senger, D.R. et al., "Vascular permeability factor (VPF, VEGF) in tumor biology", Cancer and Metastasis Reviews, vol. 12, pp. 303-324 (1993).

Shen, Y. et al., "Comparison of Electrophilic Amination Reagents for N-Amination of 2-Oxazolidinones and Application to Synthesis of Chiral Hydrazones", J. Org. Chem., vol. 67, No. 17, pp. 6236-6239 (2002).

Simone, J.V., Part XIV: Oncology, No. 154: "Introduction", Cecil Textbook of Medicine, 20th Ed., W.B. Saunders Company, publ., Bennett, J.C. et al., eds., pp. 1004-1008 (1996).

Skobe, M. et al., "Halting angiogenesis suppresses carcinoma cell invasion", Nature Medicine, vol. 3, No. 11, pp. 1222-1227 (1997).

Suzuki, M. et al., "A Convenient Synthesis of 3-Substituted Pyrrole-2,4-dicarboxylic Acid Esters", J. Org. Chem., vol. 39, No. 13, p. 1980 (1974).

Svete, J. et al., "2-Benzoyl-2-ethoxycarbonylvinyl-1 and 2-Benzoylamino-2-methoxycarbonylvinyl-1 as N-Protecting Groups in Peptide Synthesis. Their Application in the Synthesis of Dehydropeptide Derivatives Containing N-Terminal 3-Heteroarylamino-2,3-dehydroalanine", J. Heterocyclic Chem., vol. 34, pp. 177-193 (1997).

Taft, W.E. et al., "as-Triazines. I. 5-Sulfanilamido Derivatives and Intermediates", J. Med. Chem., pp. 883-887 (1967).

Terman, B.I. et al., "Identification of the KDR Tyrosine Kinase as a Receptor for Vascular Endothelial Cell Growth Factor", Biochemical and Biophysical Research Communications, vol. 187, No. 3, pp. 1579-1586 (1992).

Toplak, R. et al., "Ethyl 2-(2-Acetyl-2-ethoxycarbonyl-1-ethenyl)amino-3-dimethylaminopropenoate in the Synthesis of Heterocyclic Systems. The Synthesis of Substituted 3-Aminoazolo- and -Azinopyrimidinones, Pyridopyridinones and Pyranones", Heterocycles, vol. 50, No. 2, pp. 853-866 (1999).

West, A.R., Basic Solid State Chemistry, John Wiley & Sons Ltd., publ., pp. 356-365 (1988).

Wolff, M.E., ed., Burger's Medicinal Chemistry and Drug Discovery, 5th Ed., vol. I: Principles and Practice, John Wiley & Sons, Inc., publ., pp. 975-977 (1995).

METHODS FOR THE PREPARATION OF PYRROLOTRIAZINE COMPOUNDS

This application claims a benefit of priority from U.S. Provisional Application No. 60/599,135, filed Aug. 5, 2004, the entire disclosure of which is herein incorporated by reference.

FIELD OF THE INVENTION

The present invention relates to methods of preparing an aminated pyrrole intermediate which is useful in the preparation of pyrrolotriazine compounds. More generally, the invention further relates to methods for preparing pyrrolotriazine compounds having activity as kinase inhibitors and, in particular, to methods for making pyrrolotriazine-containing compounds useful for treating kinase-associated conditions.

BACKGROUND OF THE RELATED TECHNOLOGY

While normal angiogenesis plays an important role in several processes including embryonic development, wound healing, and female reproductive function, undesirable or pathological angiogenesis has been associated with diseases such as diabetic retinopathy, psoriasis, rheumatoid arthritis, atheroma, Kaposi's sarcoma and haemangioma, asthma, cancer, and metastatic disease.

In adults, endothelial cells have a low proliferation index with the exception of tissue remodeling, such as wound healing and the female reproductive cycle, and adipogenesis. However, in pathological states as described above, endothelial cells are actively proliferating and organizing into vessels. Upon exposure to angiogenic stimuli with growth factors, including but not limited to vascular endothelial growth factor (VEGF) and basic fibroblast growth factor (bFGF), endothelial cells re-enter the cell cycle, proliferate, migrate and organize into a three-dimensional network. It is now widely accepted that the ability of tumors to expand and metastasize is dependent upon the formation of this vascular network.

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain. Binding of a ligand to the receptor results in stimulation of the receptor-associated tyrosine kinase activity that leads to phosphorylation of tyrosine residues on both the receptor and other intracellular proteins, leading to a variety of cellular responses. To date, at least nineteen distinct RTK subfamilies, defined by amino acid sequence homology, have been identified. One of these subfamilies includes fms-like tyrosine kinase receptor, Flt or Flt1 (VEGFR-1), the kinase insert domain-containing receptor, KDR (also referred to as Flk-1 or VEGFR-2), and another fms-like tyrosine kinase receptor, Flt4 (VEGFR-3). Two of these related RTKs, Flt and KDR, have been shown to bind VEGF with high affinity. Binding of VEGF to these receptors expressed in heterologous cells has been associated with changes in the tyrosine phosphorylation status of cellular proteins and calcium fluxes. BEGF, along with acidic and basic fibroblast growth factor (aFGF and bFGF) have been identified as having in vitro endothelial cell growth promoting activity. By virtue of the restricted expression of its receptors, the growth factor activity of VEGF, in contrast to that of the FGFs, is relatively specific towards endothelial cells.

Recent evidence indicates that VEGF is an important stimulator of both normal and pathological angiogenesis and vascular permeability.

Binding of VEGF or bFGF to their corresponding receptor results in dimerization autophosphorylation on tyrosine residues and enzymatic activation. These phosphotyrosine residues serve as "docking" sites for specific downstream signaling molecules and enzymatic activation results in proliferation of endothelial cells. Disruption of these pathways should therefore result in inhibition of endothelial cell proliferation.

In addition to the aforementioned indications that can be treated with pyrrolotriazine compounds, it is noted that pyrrolotriazine compounds have been found to be useful as kinase inhibitors useful for inhibiting cell proliferation. Pyrrolotriazine compounds substituted with an acid group reportedly having $sPLA_2$-inhibitory activity are disclosed in WO 01/14378 A1 to Shionogi & Co., Ltd, published Mar. 1, 2001 in Japanese. Recently discovered pyrrolotriazine compounds are disclosed, for example in commonly assigned U.S. patent application Ser. No. 09/573,929 filed May 18, 2000 and published Application U.S. 20040072832A1, filed Jul. 18, 2003. Other compounds suitable for inhibiting kinase activity are disclosed in commonly assigned U.S. Pat. No. 6,670,357. Pyrrolotriazine compounds having activity against signal transduction, e.g. against human epidermal growth factor receptor (HER) and associated glycoproteins have been disclosed in commonly assigned U.S. application Ser. No. 10/736,476 filed Dec. 15, 2003, as well as in the aforementioned application Ser. No. 09/573,929. Pyrrolotriazine compounds having activity against cMET anti-angiogenesis growth factor receptors are disclosed in commonly assigned U.S. Provisional Application Ser. No. 60/583,459, filed Jun. 28, 2004. Each of the foregoing mentioned commonly assigned patent documents, which may disclose various synthetic methods, is herein incorporated by reference in its entirety.

Other methods for manufacturing pyrrolotriazines are disclosed in commonly assigned U.S. application Ser. No. 10/289,010 filed Nov. 6, 2002 (now issued as U.S. Pat. No. 6,867,300), and U.S. Provisional Application Ser. No. 60/584,382, filed Jun. 30, 2004. These applications describe processes for producing pyrrolotriazines using amino pyrrole intermediates. According to U.S. Pat. No. 6,867,300, for example, amino pyrrole compounds may be formed by aminating a pyrrole using a haloamine such as chloroamine. This chloramine reagent is a gaseous reactant that can present handling difficulties during the manufacturing process. U.S. Provisional Application Ser. No. 60/584,382 discloses the formation of aminated pyrrole intermediates using other aminating agents.

Additional processes are needed to produce intermediates useful in forming pyrrolotriazines, and the target compounds themselves. There is a particular need for processes that utilize commercially available starting materials in order to minimize costs and/or reduce reliance on reactants that are inefficient or undesirable for manufacturing, while maintaining acceptable product yields.

SUMMARY OF THE INVENTION

One aspect of the present invention provides a method for preparing a compound useful in the synthesis of pyrrolotriazines having the formula:

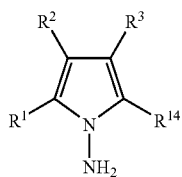

wherein $R^1$ is CHO, CN, $CO_2R^4$ or $COR^4$;
$R^2$ is $C_{1-4}$ alkyl;
$R^3$ is $C_{1-4}$ alkyl,

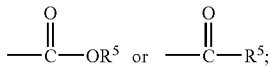

$R^4$ is $C_{1-4}$ alkyl, aryl, or $C_{1-4}$ alkoxy;
$R^5$ is $C_{1-4}$ alkyl;
$R^{14}$ is selected from hydrogen, halogen, cyano, nitro, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_f$, $SR_f$, $S(=O)R_e$, $S(=O)_2R_e$, $P(=O)_2R_e$, $S(=O)_2OR_e$, $P(=O)_2OR_e$, $NR_gR_h$, $NR_gS(=O)_2R_e$, $NR_gP(=O)_2R_e$, $S(=O)_2NR_gR_h$, $P(=O)_2NR_gR_h$, $C(=O)OR_e$, $C(=O)R_f$, $C(=O)NR_gR_h$, $OC(=O)R_f$, $OC(=O)NR_gR_h$, $NR_gC(=O)OR_e$, $NR_dC(=O)NR_gR_h$, $NR_dS(=O)_2NR_gR_h$, $NR_dP(=O)_2NR_gR_h$, $NR_gC(=O)R_f$, or $NR_gP(=O)_2Re$;
$R_d$, $R_g$ and $R_h$ are independently hydrogen, alkyl or substituted alkyl, cycloalkyl or substituted cycloalkyl, heterocycle or substituted heterocycle, or aryl or substituted aryl, or said $R_b$ and $R_c$ together with the N to which they are bonded optionally form a heterocycle or substituted heterocycle;
$R_e$ is alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl; and
$R_f$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;
including the steps of:
(a) cyclizing a compound of formula II:

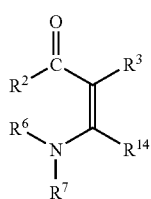

wherein:
$R^6$ is

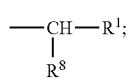

$R^8$ is H or a halogen;
$R^7$ is $NR^9R^{10}$; and
$R^9$ and $R^{10}$ are independently H, aralkyl, or together form a heteroaryl group, provided that $R^9$ and $R^{10}$ are not both H;
to form a compound of formula I:

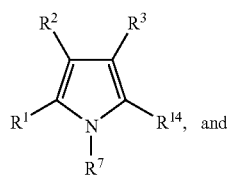

(b) deprotecting the nitrogen in $R^7$ by amination or hydrogenation to form a compound of formula III.

Another aspect of the present invention provides a method for preparing a compound useful in the synthesis of pyrrolotriazines having the formula III:

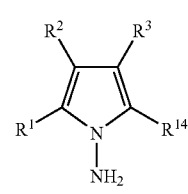

wherein $R^1$ is CHO, CN, $CO_2R^4$ or $COR^4$;
$R^4$ is $C_{1-4}$ alkyl, aryl, or $C_{1-4}$ alkoxy;
$R^2$ is $C_{1-4}$ alkyl;
$R^3$ is $C_{1-4}$ alkyl,

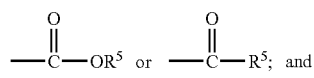

$R^5$ is $C_{1-4}$ alkyl;
$R^{14}$ is selected from hydrogen, halogen, cyano, nitro, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_f$, $SR_f$, $S(=O)R_e$, $S(=O)_2R_e$, $P(=O)_2R_e$, $S(=O)_2OR_e$, $P(=O)_2OR_e$, $NR_gR_h$, $NR_gS(=O)_2R_e$, $NR_gP(=O)_2R_e$, $S(=O)_2NR_gR_h$, $P(=O)_2NR_gR_h$, $C(=O)OR_e$, $C(=O)R_f$, $C(=O)NR_gR_h$, $OC(=O)R_f$, $OC(=O)NR_gR_h$, $NR_gC(=O)OR_e$, $NR_dC(=O)NR_gR_h$, $NR_dS(=O)_2NR_gR_h$, $NR_dP(=O)_2NR_gR_h$, $NR_gC(=O)R_f$, or $NR_gP(=O)_2Re$;
$R_d$, $R_g$ and $R_h$ are independently hydrogen, alkyl or substituted alkyl, cycloalkyl or substituted cycloalkyl, heterocycle or substituted heterocycle, or aryl or substituted aryl, or said $R_b$ and $R_c$ together with the N to which they are bonded optionally form a heterocycle or substituted heterocycle;
$R_e$ is alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl; and
$R_f$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

the method including:

(a) preparing a compound of formula II:

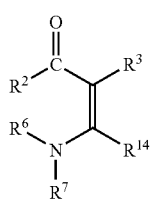

II wherein:
$R^6$ is

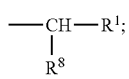

$R^8$ is H or a halogen;
$R^7$ is $NR^9R^{10}$; and
$R^9$ and $R^{10}$ are independently H, aralkyl, or together form a heteroaryl group, provided that $R^9$ and $R^{10}$ are not both H;

the preparing of step (a) being a method selected from:
(i) forming a compound of formula IV:

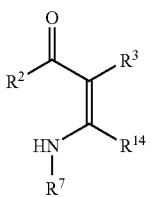

IV by reacting a mono-, di-, or tri-substituted hydrazine with a compound selected from the group consisting of:

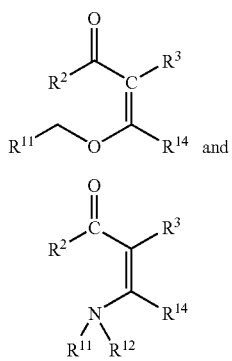

VIIIa

VIIIb wherein $R^{11}$ and $R^{12}$ are independently $C_{1-4}$ alkyl, followed by reacting said compound of formula IV with a reagent $XR^6$, wherein X is halogen and $R^6$ is as defined above; and (ii) reacting a compound of formula

with a compound selected from the group consisting of:

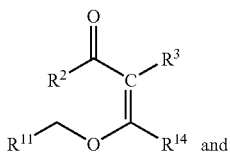

VIIIa

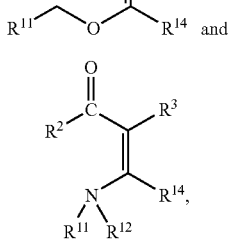

VIIIb (b) cyclizing said compound of formula II to form a compound of formula I:

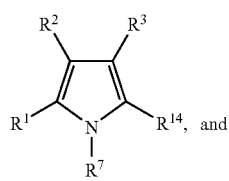

I (c) deprotecting the ring nitrogen atom in the compound of formula I by amination or hydrogenation to form compound III.

A further aspect of the present invention provides a method of preparing a pyrrolotriazine of the following formula VII:

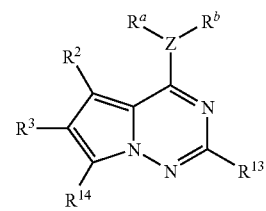

VII wherein
$R^2$ is $C_{1-4}$ alkyl;
$R^3$ is selected from $C_{1-4}$alkyl,

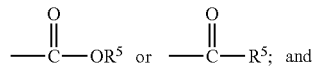

$R^5$ is $C_{1-4}$alkyl;
$R^{13}$ is selected from H, alkyl or aryl;

Z is selected from O, S, N, and halogen, with the provisos that (a) when Z is O or S, $R^b$ is absent and (b) when Z is halogen, both $R^a$ and $R^b$ are absent;

$R^a$ is selected from hydrogen, substituted aryl, including aryl substituted with $NHSO_2$alkyl, substituted heteroaryl, and optionally substituted bicyclic 7-11 membered saturated or unsaturated carbocyclic or heteroaryl ring; and $R^b$ is selected from the group consisting of hydrogen, alkyl, and substituted alkyl or is absent;

comprising the steps of
(a) preparing a compound of formula II:

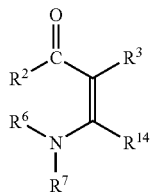

II wherein:
$R^6$ is

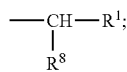

$R^8$ is H or a halogen;
$R^7$ is $NR^9R^{10}$; and
$R^9$ and $R^{10}$ are independently H, aralkyl, or together form a heteroaryl group, provided that $R^9$ and $R^{10}$ are not both H;

said preparing comprising a method selected from the group consisting of:
(i) reacting a mono-, di-, or tri-substituted hydrazine with a compound selected from the group consisting of:

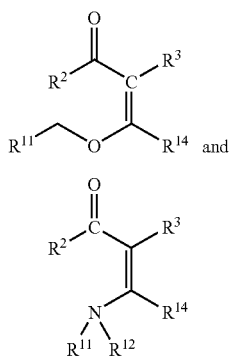

VIIIa

VIIIb wherein $R^{11}$ and $R^{12}$ are independently $C_{1-4}$ alkyl, and reacting said compound of formula IV with $XR^6$, wherein X is halogen; and
(ii) reacting a compound of formula

with a compound selected from the group consisting of:

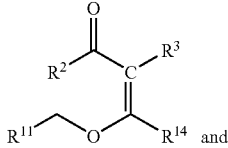

VIIIa

VIIIb (b) cyclizing said compound of formula II to form a compound of formula I:

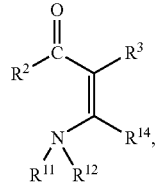

I (c) deprotecting the nitrogen in $R^7$ by amination or hydrogenation to form compound III:

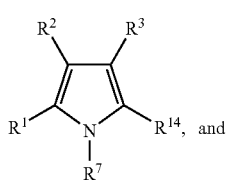

III wherein $R^1$ is CHO, CN, $CO_2R^4$ or $COR^4$;
$R^4$ is $C_{1-4}$ alkyl, aryl, or $C_{1-4}$ alkoxy; $R^2$ is $C_{1-4}$ alkyl,

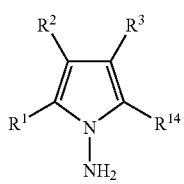

and $R^5$ is $C_{1-4}$ alkyl;
(d) cyclizing said compound of formula III to form a compound of formula V:

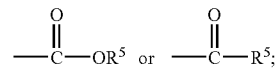

V

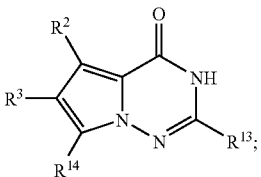

using an amide of formula $R^{13}(CO)NH_2$; wherein $R^{13}$ is selected from H, alkyl or aryl;

(e) halogenating the compound of formula V to form a compound of formula VI:

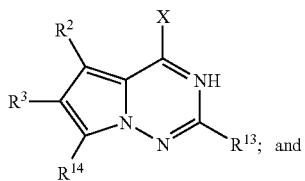

(f) reacting the compound of formula VI with B-ZR$^a$R$^b$, wherein B is selected from the group consisting of H, optionally substituted alkyl, and optionally substituted cycloalkyl, to form a pyrrolotriazine of formula VII. Generally, cyclization to form the compound may be conducted by various means, as discussed infra.

DETAILED DESCRIPTION OF THE INVENTION

The present invention provides a method of preparing a pyrrolotriazine compound of formula VII:

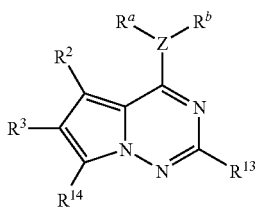

wherein
R$^2$ is C$_{1-4}$ alkyl;
R$^3$ is C$_{1-4}$ alkyl,

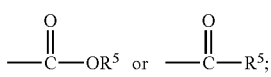

R$^5$ is C$_{1-4}$ alkyl;
R$^{13}$ is selected from H, alkyl or aryl;
R$^{14}$ is selected from hydrogen, halogen, cyano, nitro, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, OR$_f$, SR$_f$, S(=O)R$_e$, S(=O)$_2$R$_e$, P(=O)$_2$R$_e$, S(=O)$_2$OR$_e$, P(=O)$_2$OR$_e$, NR$_g$R$_h$, NR$_g$S(=O)$_2$R$_e$, NR$_g$P(=O)$_2$R$_e$, S(=O)$_2$NR$_g$R$_h$, P(=O)$_2$NR$_g$R$_h$, C(=O)OR$_e$, C(=O)R$_f$, C(=O)NR$_g$R$_h$, OC(=O)R$_f$, OC(=O)NR$_g$R$_h$, NR$_g$C(=O)OR$_e$, NR$_d$C(=O)NR$_g$R$_h$, NR$_d$S(=O)$_2$NR$_g$R$_h$, NR$_d$P(=O)$_2$NR$_g$R$_h$, NR$_g$C(=O)R$_f$, or NR$_g$P(=O)$_2$R$_e$;
R$^a$ is selected from hydrogen, substituted aryl, including aryl substituted with NHSO$_2$alkyl, substituted heteroaryl, and optionally substituted bicyclic 7-11 membered saturated or unsaturated carbocyclic or heteroaryl ring;
R$^b$ is selected from the group consisting of hydrogen, alkyl, and substituted alkyl or is absent;
R$_d$, R$_g$ and R$_h$ are independently hydrogen, alkyl or substituted alkyl, cycloalkyl or substituted cycloalkyl, heterocycle or substituted heterocycle, or aryl or substituted aryl, or said R$_b$ and R$_e$ together with the N to which they are bonded optionally form a heterocycle or substituted heterocycle;
R$_e$ is alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl; and
R$_f$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;
Z is selected from O, S, N, and halogen, with the provisos that when Z is O or S, R$^b$ is absent and when Z is halogen, both R$^a$ and R$^b$ are absent;
Desirably, Z is O and R$^a$ is either:

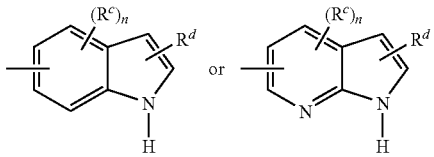

wherein n is 0, 1, or 2;
each R$^c$ is independently selected from the group consisting of H, F, Cl, and CH$_3$; and
R$^d$ is H or CH$_3$. Desirably, R$^c$ is F.

A method of preparing a pyrrolotriazine according to the invention incorporates preparation of a compound of formula III:

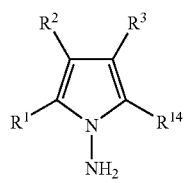

wherein R$^1$ is CHO, CN, CO$_2$R$^4$ or COR$^4$;
R$^2$, R$^3$ and R$^{14}$ are as defined above; and
R$^4$ is C$_{1-4}$ alkyl, aryl, or C$_{1-4}$ alkoxy;

by cyclizing a compound of formula II:

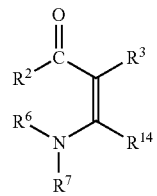

wherein:
R$^6$ is

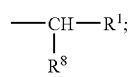

$R^8$ is H or a halogen;
$R^7$ is $NR^9R^{10}$; and
$R^9$ and $R^{10}$ are independently H, aralkyl, or together form a heteroaryl group, provided that $R^9$ and $R^{10}$ are not both H; and and deprotecting the nitrogen in $R^7$ to form the compound of formula III.

For the purposes of the present invention, the following definitions apply:

The term "alkyl", either alone or as part of another group, is meant to include optionally substituted, straight and branched chain saturated hydrocarbon groups. The term "cycloalkyl" means carbocyclic alkyl groups having from 3 to 8 carbon atoms in the ring structure.

The term "aryl" refers to monocyclic or bicyclic aromatic hydrocarbon groups having 6 to 12 carbon atoms in the ring portion, such as phenyl, naphthyl, and biphenyl groups each of which may be substituted. Aryl substituted by $NHSO_2$alkyl is also mentioned herein as a possible aryl substituent, however any specific reference to this functional group is not intended to in any way limit the scope of other contemplated substitutions with respect to the aryl species.

The term "alkoxy" is meant to include an alkyl group as defined above, which is bonded through an oxygen atom.

The term "aralkyl" is meant to include an aryl group bonded directly through an alkyl group. A non-limiting example is benzyl.

The term "heteroaryl" refers to an optionally substituted aromatic group which is a 4 to 7 membered monocyclic, 7 to 11 membered bicyclic or 10 to 15 membered tricyclic ring system, which has at least one hetero atom and at least one carbon atom-containing ring. Examples include pyridine, tetrazole, indazole, and indole.

The term "hydrazine" is meant to include compounds of the general formula $H_2NNH_2$, wherein one or more hydrogen may be substituted.

When a group is substituted, it will include one or more substituents which may be selected from halogen, hydroxyl, alkoxy, alkanoyl, alkanoyloxy, amino, alkylamino, dialkylamino, thiol, alkylthio, alkylthiono, alkylsulfonyl, sulfamido, nitro, cyano, carboxy, carbamyl, substituted carbamyl, guanidine and heterocylco, e.g. imidazolyl, furyl, thienyl, thiazolyl, pyrroliyl, pyridyl, pyrimidyl, combinations of the foregoing, and the like.

The term "cyclizing" is meant to include the formation of a ring structure through any chemical reaction, for example by addition and/or substitution reactions. In reference to cyclizing of the pyrrolotriazine, the term encompasses any reactions that result in the formation of a 5- or 6-membered ring structure adjunctly connected to the pyrrole ring.

The compounds of formula II may be synthesized by a variety of methods, two examples of which are described herein below. The first example includes the reaction of a mono-, di-, or tri-substituted hydrazine with a compound of either formula VIIIa or VIIIb:

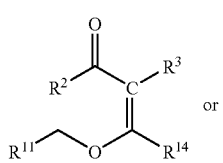
VIIIa

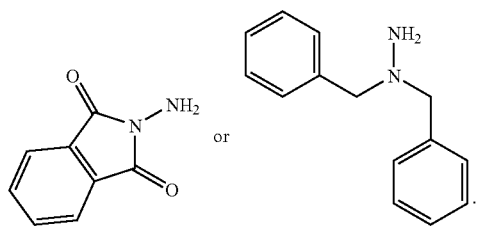
VIIIb followed by reaction with $XR^6$, wherein X is halogen. Desirably, the hydrazine is of the formula $NH_2R^7$. More desirably, the hydrazine is of the formula:

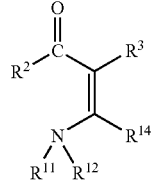

An additional, alternative preparation of a compound of formula II includes the reaction of a compound of formula

with a compound of either formula VIIIa or VIIIb.

Desirably, the compound of formula II corresponds to one of the following:

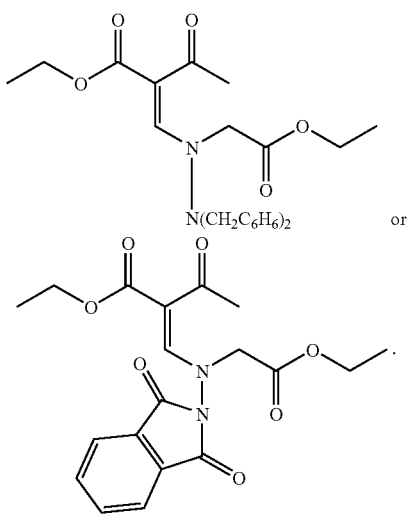

The compounds of formulas VIIIa and VIIIb may be prepared from a compound of formula IX:

IX

For example, reaction of the compound of formula IX in the presence of a trialkyl orthoformate, such as triethyl orthoformate, and acetic anhydride will produce the compound of formula VIIIa, where $R_{14}$=H. Reaction of the compound of formula IX in the presence of dimethylformamide dimethyl acetal or other dimethylformamide dialkyl acetals, where for example alkyl equals ethyl, propyl, butyl, pentyl, cyclohexyl, benzyl, will produce the compound of formula VIIIb, where $R_{14}$=H.

The cyclization of a compound of formula II to form the intermediate compound of formula III may be effected by the use of any known reagent for that purpose. Examples of suitable reagents include potassium-tert-pentylate and the combination of 1,8-diazabicyclo[5.4.0]undec-7-ene and ethyl trifluoroacetate. Another suitable mechanism includes methylation of a compound of formula II with dimethylformamide dimethyl acetal followed by cyclizing in the presence of acetic anhydride or trifluoroacetic acid.

In certain embodiments, the compound of formula III corresponds to the formula:

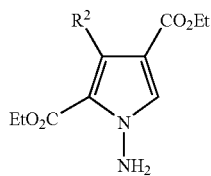

wherein $R^2$ is $C_{1-4}$ alkyl.

One method for the preparation of a desired pyrrolotriazine compound is shown in Scheme 1:

Scheme 1

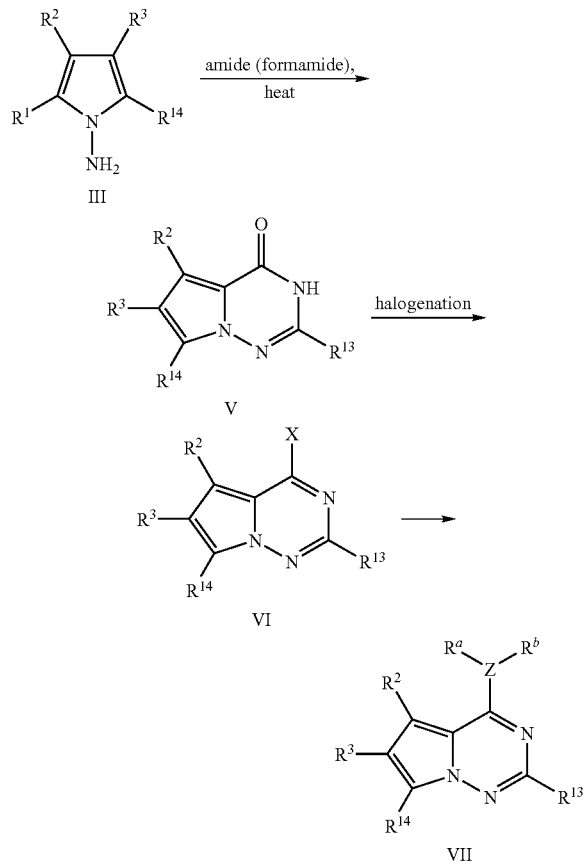

First, the compound of formula III is cyclized by treatment with an amide suitable to effect cyclization in the presence of a base such as sodium methoxide (NaOMe) or an organic acid or mineral acid such as acetic acid or phosphoric acid, respectively, with heating to form the compound of formula V. A suitable amide is formamide, however other amides may be used as alternatives to the formamide reagent, in which circumstance the resulting compound of formula V would include a corresponding substituent on the triazine ring. In that respect, a substituted amide $R^xCONH_2$ would generate the structure:

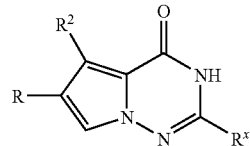

corresponding to formula V, wherein $R^x$ is may be selected from H, alkyl, cycloalkyl or aryl. Exemplary amides which may be useful for the cyclization step include formamide, carbamide (urea), alkylamides having straight, branched or cyclic alkyl substituents, and optionally substituted benzamides.

The compound of formula V is then halogenated, for example, with phosphorus oxychloride at an elevated temperature to form the compound of formula VI.

Finally, the compound of formula VI is reacted with an amine such as aniline or a phenol, in an organic solvent, such as acetonitrile or dimethylformamide (DMF), to form the desired pyrrolotriazine of formula VII.

Another method of preparing a desired compound of formula VII is shown in Scheme 2:

Scheme 2

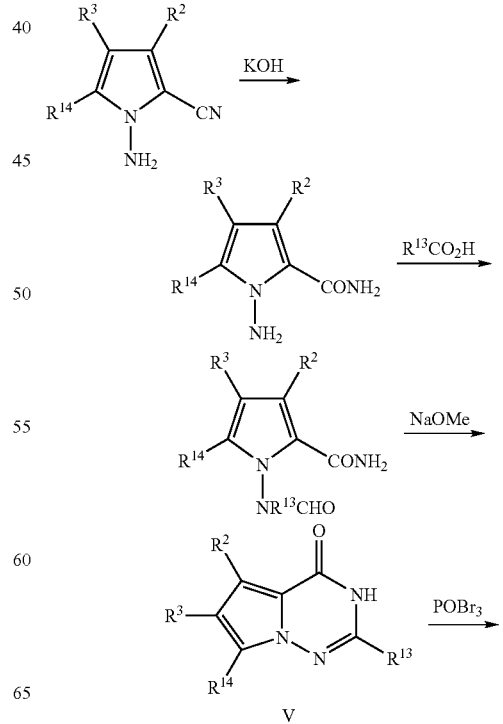

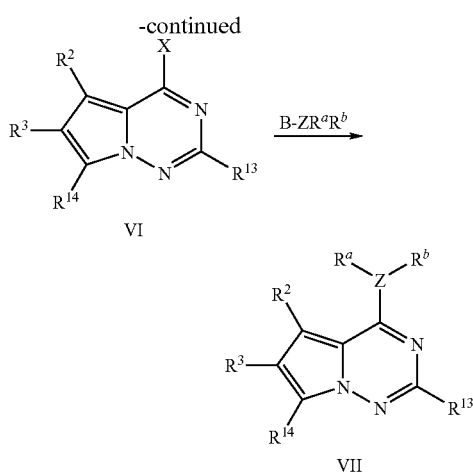

The starting material is a compound of formula III wherein $R^1$ is CN. In this preparation, the compound of formula III is reacted with an aqueous base such as KOH at room temperature to convert the nitrile substituent to an amide. This product is then reacted with an acylating agent, such as formic acid, in an aqueous solvent. The product of this reaction is then cyclized with a base such as sodium methoxide in methanol with heating to form a compound of formula V, typically wherein $R^{13}$ is H. Other substituted carboxylic acids maybe be used, such as acetic acid or benzoic acid, to afford $R_{13}$ as an alkyl or aryl group, respectively. Within the definitions provided herein for alkyl and aryl groups may also be included even more complex carboxylic acids such as amino acids.

The compound of formula V is halogenated, for example with phosphorus oxybromide at an elevated temperature, to form the compound of formula VI.

The compound of formula VI is then reacted with an amine, such as aniline, or with an alcohol such as a phenol (for example as might be utilizable in Scheme 2, above), or other suitably substituted nucleophile in a suitable solvent (e.g. acetonitrile), to form the desired pyrrolotriazine of formula VII.

Various descriptions of the preparation of compounds on the order of formula VII are described in those documents which have been previously cited and incorporated by reference, such as U.S. Pat. No. 6,867,300.

The compounds prepared according to the invention may be useful as kinase inhibitors. As mentioned above, such compounds may function as inhibitors of pathological angiogenesis and endothelial cell proliferation associated with tumor development. Also, as described in U.S. Pat. No. 6,670,357 previously herein incorporated by reference, compounds of Formula (VII) have for example been shown to be useful in treating other kinase-associated conditions including, but not limited to, inflammatory diseases, oncology diseases, autoimmune diseases, destructive bone disorders, proliferative disorders, angiogenic disorders, infectious diseases, neurodegenerative diseases, and viral diseases. More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, scleroderma, chronic thyroiditis, Grave's disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoisosis, bone resorption disease, allograft rejections, fever and myalgias due to infection, cachexia secondary to infection, meloid formation, scar tissue formation, ulcerative colitis, pyresis, influenza, osteoporosis, osteoarthritis and multiple myeloma-related bone disorder, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS<ARC or malignancy, and herpes; stroke, myocardial ischemia, ischemia in stroke heart attacks, organ hyposia, vascular hyperplasia, cardiac and renal reperfusion injury, thrombosis, cardiac hypertrophy, thrombin-induced platelet aggregation, endotoxemia and/or toxic shock syndrome, and conditions associated with prostaglandin endoperoxidase syndase-2.

The methods of manufacture of compounds for these uses as well as in the treatment of the aforementioned kinase-associated disorders present certain advantages in that they allow for the utilization of readily available starting materials that can be easily obtained and handled on a large production scale. The features and advantages of the preparation methods according to the present invention are more fully shown by the following examples, which are provided for purposes of illustration and are not to be construed as limiting the invention in any way.

EXAMPLES

Example 1

Synthesis of Dibenzylhydrazine Glycine

| | Bn$_2$NNH$_2$ | BrCH$_2$CO$_2$Et | Et$_3$N | TBAI | THF |
|---|---|---|---|---|---|
| mw | 212.29 | 167.00 | 101.19 | 369.37 | |
| g | 5.30 | 3.97 | 2.41 | 0.46 | |
| mmol | 25.0 | 23.8 | 23.8 | 1.25 | |
| mL | | 2.64 | 3.32 | | 50 |
| Density | | 1.506 | 0.726 | | |
| Conc. | | | | | |

To a solution of dibenzylhydrazine (5.30 g, 25.0 mmol) and THF (50 mL) and TBAI (0.46 g, 1.25 mmol) was added BrCH$_2$CO$_2$Et (2.64 mL, 23.8 mmol) and Et$_3$N (3.32 mL, 23.8 mmol). The reaction mixture was stirred at 60° C. for 7 hours, an additional 0.3 eq. of base and electrophile were added (BrCH$_2$CO$_2$Et, 0.83 mL, 7.5 mmol and Et$_3$N, 1.0 mL, 7.5 mmol). The reaction mixture was held overnight at R/T, an additional 0.3 eq. of each reagent was added and the reaction mixture was stirred at 60° C. for 4 more hours. The reaction mixture was partitioned with CH$_2$Cl$_2$, and the isolated organic fraction was washed with brine three (3 times), dried over Na$_2$SO$_4$, and concentrated in vacuo to afford 7.21 g, 24.2 mmol, (97%) of a crude oil.

Example 2

Synthesis of Aminopyyrole Precursor

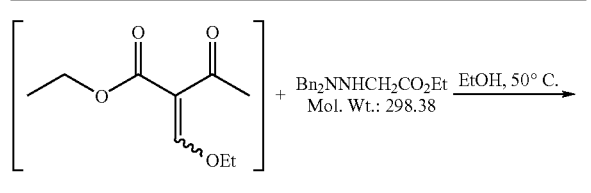

| | enol ether | dibenzylhydrazine glycine | EtOH |
|---|---|---|---|
| mw | 186 | 298 | |
| g | ~2.50 | 3.73 | |
| mmol | ~13.4 | 12.50 | |
| mL | | | 25.0 |
| density | | | |
| Conc. | | | |

A solution of crude enol ether (~2.50 g, ~13.4 mmol) and crude dibenzylhydrazine glycine (3.73 g, 12.5 mmol) in EtOH (25.0 mL). The reaction mixture was heated at 55° C. for five hours, but after 3 hours an additional 0.3 g of enol ether was added. The reaction mixture was partitioned between ethyl acetate (EtOAc) and saturated NaHCO$_3$(aq). The product-containing fraction was washed with saturated NaHCO$_3$(aq) followed by brine, and dried over MgSO$_4$ before being concentrated in vacuo. The resulting crude yield was 4.25 g, 9.7 mmol (72%). The crude product was subsequently purified by column chromatography (60% EtOAc in hexanes) to afford 1.96 g, 4.47 mmol, in a yield of 33%.

Example 3

Bn$_2$N-Pyrrole Cyclization (Formula I)

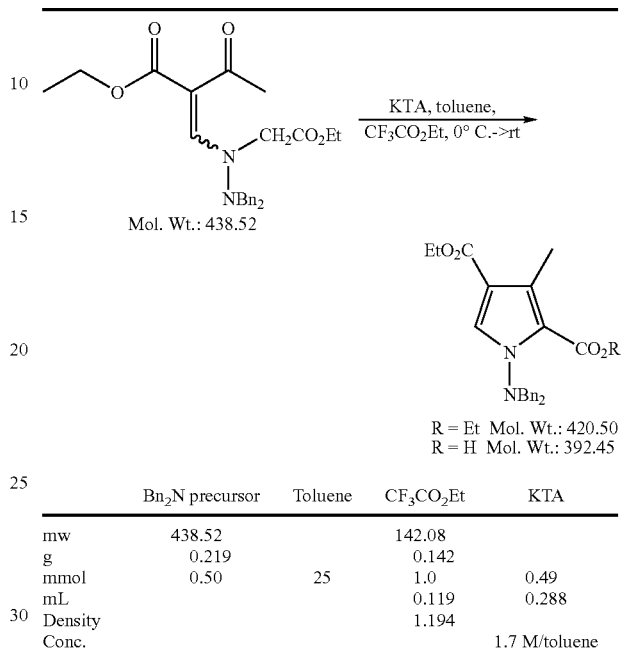

| | Bn$_2$N precursor | Toluene | CF$_3$CO$_2$Et | KTA |
|---|---|---|---|---|
| mw | 438.52 | | 142.08 | |
| g | 0.219 | | 0.142 | |
| mmol | 0.50 | 25 | 1.0 | 0.49 |
| mL | | | 0.119 | 0.288 |
| Density | | | 1.194 | |
| Conc. | | | | 1.7 M/toluene |

Potassium t-amylate (0.29 mL, 0.49 mmol, 1.7M/toluene) was added to a solution of the dibenzylamine pyrrole precursor (0.22 g, 0.50 mmol) and ethyl trifluroacetate in touleune (25 mL). The reaction mixture was stirred at 0° C. for two hours, HPLC analysis indicated 50% conversion, a second equivalent of KTA was added and the reaction mixture was left overnight at R/T. The next morning LC/MS analysis indicated that it was not unreacted starting material but hydrolyzed product (R=H). The reaction was quenched with saturated NH$_4$Cl(aq), followed by extraction with EtOAc. The combined organic extracts were washed with brine, dried over MgSO$_4$, and concentrated in vacuo to afford 0.25 g of the crude product.

Example 4

Deprotection of Bn$_2$N-Pyrrole

| | Bn$_2$N-pyrrole | Pd/C | EtOH |
|---|---|---|---|
| mw | R = H –392 | | |
| | R = Et –420 | | |
| g | 0.082 | 0.082 | |

-continued

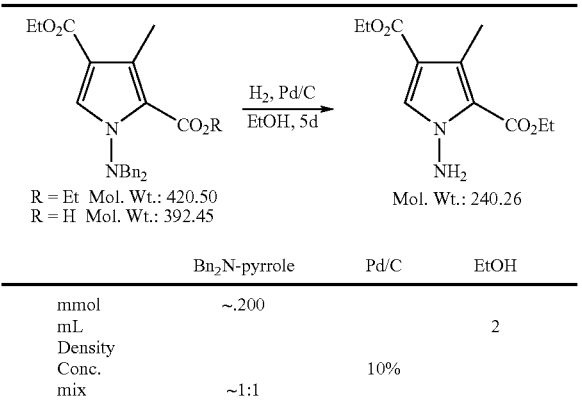

R = Et Mol. Wt.: 420.50
R = H Mol. Wt.: 392.45

Mol. Wt.: 240.26

|  | Bn$_2$N-pyrrole | Pd/C | EtOH |
|---|---|---|---|
| mmol | ~.200 | | |
| mL | | | 2 |
| Density | | | |
| Conc. | | 10% | |
| mix | ~1:1 | | |

Pd/C (0.082 g, ~0.08 mmol, 10 wt %) was added to a N$_2$ blanketed solution of Bn$_2$N-pyrrole (0.082 g, 0.20 mmol) and EtOH (2.0 mL). The N$_2$ atmosphere was replaced with a balloon of H$_2$, and the reaction mixture was stirred at R/T for 48 hours; an additional 0.082 g of Pd/C 10% was added to the reaction mixture and the H$_2$ atmosphere was maintained. After an additional 24 hours, a third charge of Pd/C (0.082 g) was added and the reaction mixture was stirred under H$_2$ over an additional two days. The reaction mixture was filtered through SiO$_2$ concentrated in vacuo and purified by column chromatography. It appeared that the carboxylic acid was slowly converted to the ester under the reaction conditions. Yield: 0.034 g, 0.142 mmol, 71%.

Example 5

Addition of Substituted Hydrazine to Enol Ether

Reagents (ethyl acetoacetate, acetic anhydride, and triethylorthoformate) were combined at R/T under N$_2$. The reaction mixture was refluxed for 4 hours and cooled to rt, and used as is.

Reaction A.

10 mL≈21 mmol of the enol ether solution was added to solid H$_2$N-NPhth (162 g/mmol≈3.40 g≈21 mmol). The reaction mixture was stirred briefly in a test tube with a screw cap. The reaction mixture became very tacky and after standing for one hour with occasional manual agitation was partitioned between CH$_2$Cl$_2$ (150 mL) and water (20 mL). The organic layer was washed once with saturated NaHCO$_3$(aq) and then with water, dried over Na$_2$SO$_4$ and concentrated to about 50 m/L triturated with heptane (~100 mL). The solid was isolated by filtration yield 4.92 g, (78%) over two steps.

Reaction B.

10 mL≈21 mmol of the enol ether was added to solid H$_2$N NBn$_2$ (212 g/mmol≈4.45 g ≈21 mmol). The reaction mixture was stirred at R/T in a screw cap test tube for one hour, partioned between EtOAc (50 mL) and H$_2$O (20 mL). The organic layer was washed two times with 20 mL saturated NaHCO$_3$(aq). The aqueous layer was back extracted 1×15 mL EtOAc. The combined organic layer were washed with brine, dried over Na$_2$SO$_4$ and concentrated in vacuo. The dark oil was passed through a plug of SiO$_2$ (9:1 hexanes/EtOAc). The collected organic fractions were concentrated under reduced pressure to afford an amber oil, yield 6.48 g, 18.4 mmol, (88%).

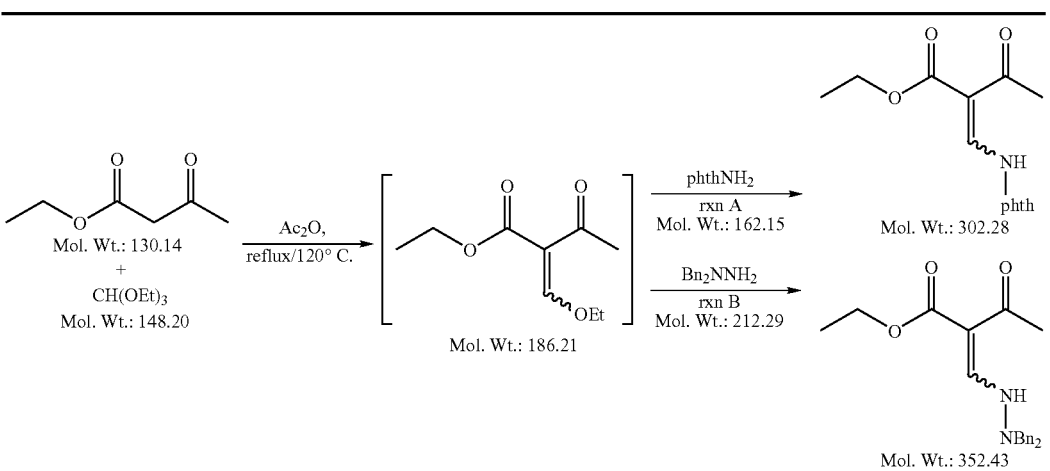

|  | Ethyl acetoacetate | acetic anhydride | Triethylorthoformate | Aminophthalimide | N,N-dibenzylhydrazine |
|---|---|---|---|---|---|
| mw | 130.14 | 102.09 | 148.20 | 162.15 | 212.29 |
| g | 130.14 | 204.18 | 148.20 | 3.40 | 4.45 |
| mmol | 1.0 | 2.0 | 1.0 | 21 | 21 |
| mL | 126 | 188 | 166 | | |
| Density | 1.029 | 1.087 | 0.891 | | |
| Conc. | | | | | |

Example 6

Alternative Procedure for the Addition of Dibenzylhydrazine

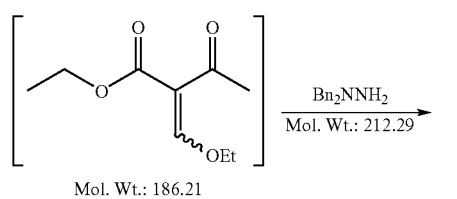

To a 25 mL solution of neat enol ether (2.1M) was added 11.2 g of N,N-dibenzylhydrazine. The reaction mixture was stirred under $N_2$ for one hour, and partition between saturated $NaH_2PO_4$/saturated $Na_2HPO_4$ (1:1) 50 mL and EtOAc 35 mL. The organic layer was washed with water, dried over $Na_2SO_4$ and concentrated in vacuo. Yield: 16.8 g, 47.7 mmol, 91%.

Example 7

Alkylation of Aminophthalimide

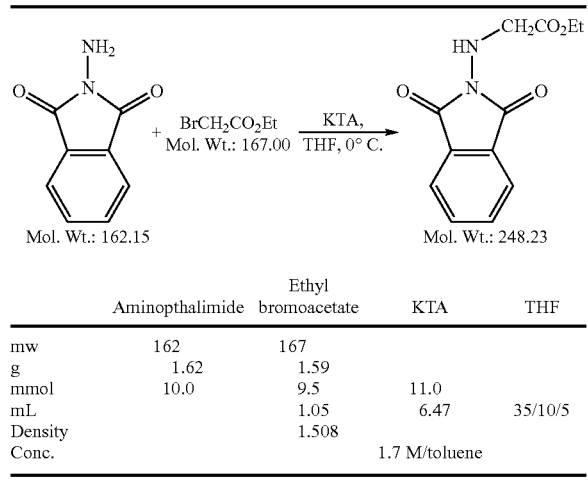

|  | Aminopthalimide | Ethyl bromoacetate | KTA | THF |
|---|---|---|---|---|
| mw | 162 | 167 | | |
| g | 1.62 | 1.59 | | |
| mmol | 10.0 | 9.5 | 11.0 | |
| mL | | 1.05 | 6.47 | 35/10/5 |
| Density | | 1.508 | | |
| Conc. | | | 1.7 M/toluene | |

To a 0° C. solution of aminophthalimide (1.62 g, 10.0 mmol) and THF (35 mL) was added KTA (6.47 mL, 11.0 mmol). The reaction mixture was stirred at 0° C. for 1.5 hours then treated slowly with ethyl bromoacetate (1.05 mL, 9.5 mmol) as a solution in THF (10.0 mL). The reaction mixture was stirred at 0° C. for an additional 6 hours, then warmed to R/T overnight. The reaction mixture was diluted with saturated $NH_4Cl(aq)$, and partitioned with $CH_2Cl_2$. The isolated aqueous phases was further extracted with the same organic solvent. The combined organic extracts were washed with saturated $NaHCO_3(aq)$, washed with brine, and dried over $Na_2SO_4$. For purification, the crude product was subjected to preparative TLC with 40% EtOAc in hexanes as the solvent medium, followed by column chromatography using 20%-40% EtOAc in hexanes. The isolated product was then recrystallized from EtOAc/hexanes to afford 0.747 g, of the desired product in 32% yield.

Example 8

Alkylation of Aminophthalimide Derivative

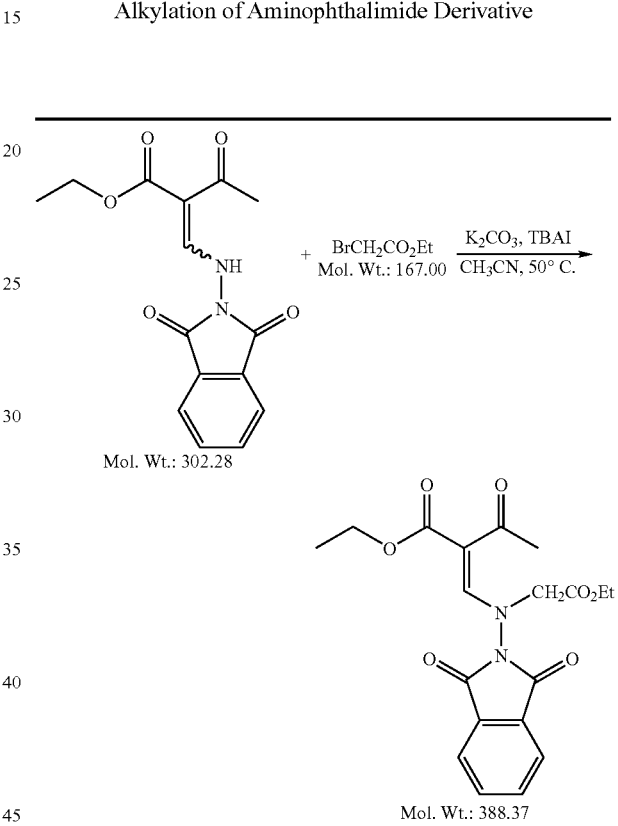

|  | Aminophthalimide derivative | Ethyl bromoacetate | $K_2CO_3$ | $CH_3CN$ | TBAI |
|---|---|---|---|---|---|
| mw | 302 | 167 | 138 | | 369 |
| g | 1.52 | 1.68 | 0.728 | | 0.184 |
| mmol | 5.02 | 10.04 | 5.27 | | 0.5 |
| mL | | 1.11 | | 25 | |
| Density | | 1.506 | | | |
| Conc. addition at ~5 hrs. | | 0.3 mL | 0.24 g | | |

$BrCH_2CO_2Et$ (1.68 g, 1.11 mL, 10.0 mmol) was added to a slurry suspension of aminophthalimide derivative (1.52 g, 5.02 mmol), $K_2CO_3$ (0.728 g, 5.27 mmol), TBAI (0.184 g, 0.50 mmol) in $CH_3CN$ (25 mL). The reaction mixture was stirred at 50° C. under $N_2$ for 5 hours, before an additional 0.3 mL of $BrCH_2CO_2Et$ and 0.24 g $K_2CO_3$ were added. The reaction mixture became more homogenous over the next 1.5 hours. For the work-up, the reaction mixture was partitioned between brine/EtOAc and the isolated aqueous phase was extracted with EtOAc. The combined organic phases were washed with saturated NH₄Cl(aq), washed with brine, dried over Na₂SO₄ and concentrated in vacuo. The crude product was crystallized using EtOAc/hexanes, to afford 1.02 g, 2.63 mmol in 52% yield.

Example 9

Alternative Pyrrole Synthesis

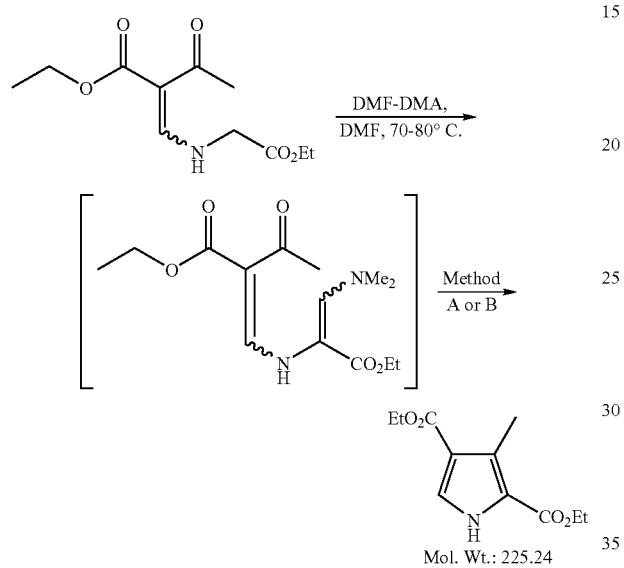

| | Pyrrole precursor | DMF-DMA | DMF | AcOH | TFAA |
|---|---|---|---|---|---|
| mw | 243 | 119 | | | 210.03 |
| g | 4.86 | 7.14 | | | 4.461 |
| mmol | 20 | 60 | 20 | | 21.2 |
| mL | | 7.96 | | 4.5 | 3.0 |
| Density | | 0.897 | | | 1.487 |
| Conc. | | | | | |

The reagents were combined and heated under N₂ at 70-80° C. for 2.5 hours. The DMF and excess DMF-DMA were removed by high vacuum distillation. Product solidified on standing over the weekend.

Method A. To the eneamine intermediate (0.490 g, 1.5 mmol) was added glacial acetic acid (4.5 mL). The reaction mixture was heated at reflux for 2.5 hours. The reaction mixture was cooled to R/T, partitioned between saturated NaHCO3(aq), and toluene, dried over Na₂SO₄ and concentrated in vacuo to yield 0.26 g (1.16 mmol), 77%.

Method B. To the intermediate eneamine (0.894 g, 3.0 mmol) was added trifluroacetic anhydride (3 mL). The reaction mixture was stirred at R/T for 2 hours, quenched with 1.5 ml of EtOH and left over the weekend. The resulting crystallatine was isolated by vacuum filtration and washed with heptane.

Example 10

Alternative Phthalimide Pyrrole Synthesis

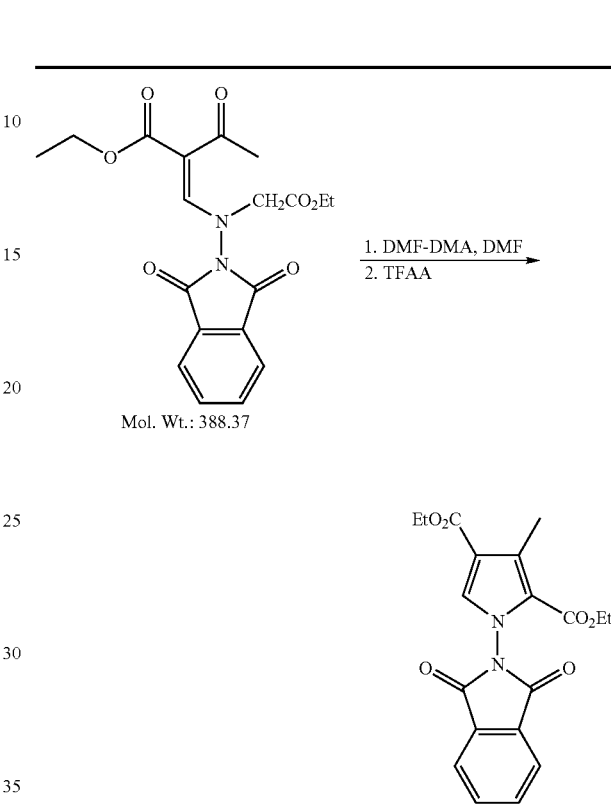

| | Pyrrole precursor | DBU | CH₂Cl₂ | TFAA |
|---|---|---|---|---|
| mw | 388 | 152.24 | | 210.03 |
| g | 0.097 | 0.038 | | 0.053 |
| mmol | 0.25 | 0.25 | | 0.25 |
| mL | | 0.037 | 2.0 | 0.035 |
| Density | | 1.018 | | 1.487 |
| Conc. | | | | |

To a 0° C. solution of phthalimide pyrrole precursor (0.097 g, 0.25 mmol) in CH₂Cl₂ (2.0 mL) was added DBU (0.037 mL, 0.25 mmol). This reaction mixture became a dark orange in about 10 minutes. The reaction mixture was stirred at 0° C. for an additional 20 minutes and treated with TFAA (0.035 mL, 0.25 mmol). The reaction mixture was stirred at 0° C. for 2.5 hours, then treated with a second equivalent of TFAA. The reaction was warmed to R/T overnight and concentrated in vacuo. The crude product was subjected to chromatography with 20-40% EtOAc/hexanes and then recrystallized from EtOAc/hexanes to afford 0.068 g, 0.184 mmol, in 75% yield.

Example 11

Synthesis of Phthalimide Pyrrole Precursor

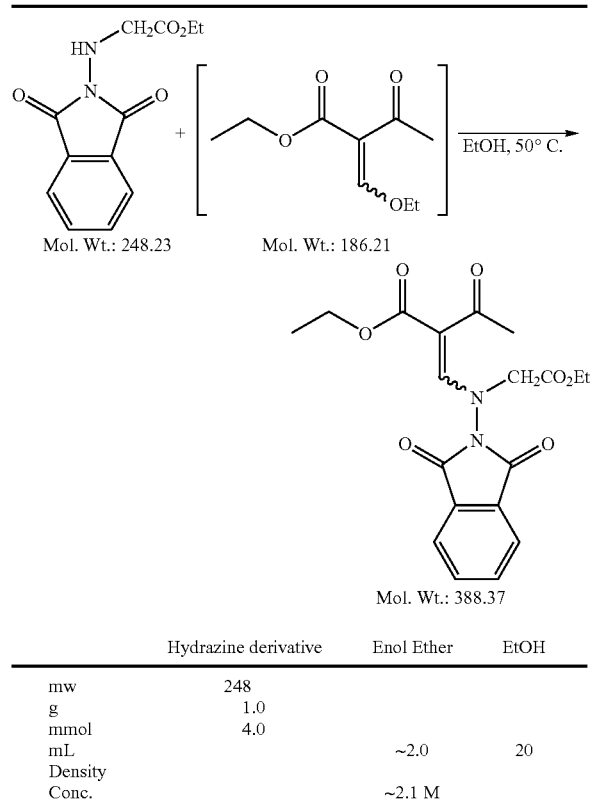

|  | Hydrazine derivative | Enol Ether | EtOH |
|---|---|---|---|
| mw | 248 |  |  |
| g | 1.0 |  |  |
| mmol | 4.0 |  |  |
| mL |  | ~2.0 | 20 |
| Density |  |  |  |
| Conc. |  | ~2.1 M |  |

The reaction mixture was stirred at 50° C. for 24 hours. An additional 1 eq. of enol ether was added and the reaction mixture was heated to 80° C. After an additional 6 hours a third eq of the enol was added and the reaction mixture was left at R/T for total of 4 days. The reaction mixture was filtered, and washed with 50% EtOH/water to afford 0.45 g, 1.16 mmol, in 30% yield.

Example 12

Deprotection of Phthalimide Pyrrole

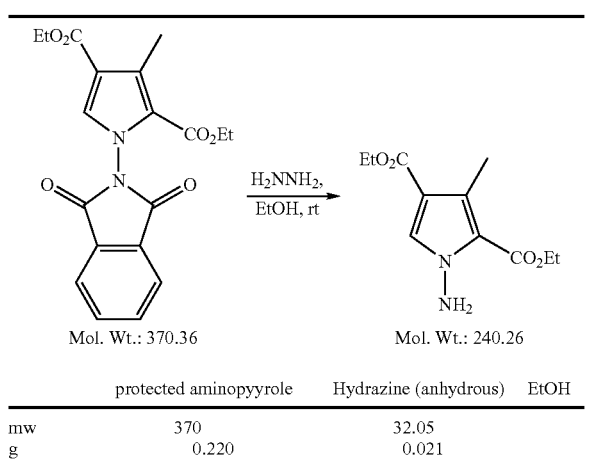

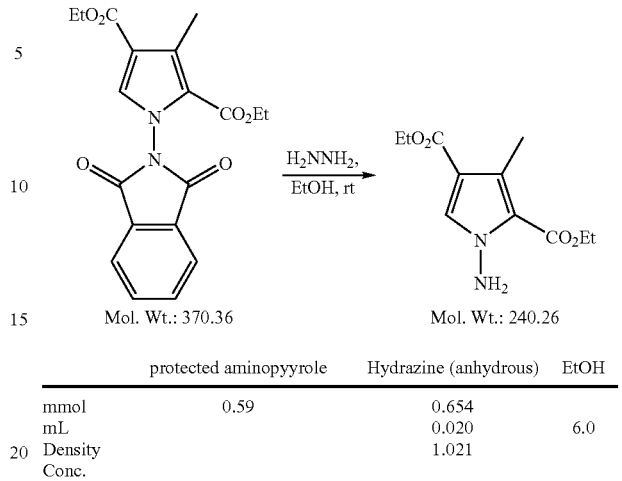

|  | protected aminopyyrole | Hydrazine (anhydrous) | EtOH |
|---|---|---|---|
| mw | 370 | 32.05 |  |
| g | 0.220 | 0.021 |  |
| mmol | 0.59 | 0.654 |  |
| mL |  | 0.020 | 6.0 |
| Density |  | 1.021 |  |
| Conc. |  |  |  |

To a R/T solution of crude protected aminopyrrole (0.220 g, 0.59 mmol) in EtOH (6.0 mL) was added anhydrous hydrazine (0.021 mL, 0.65 mmol). The reaction mixture became markedly dark in color, as the reaction progressed a precipitate was evident and the reaction became pale yellow in color. The reaction mixture was left overnight, filtered, quenched with 10% HCl(aq), and partitioned with EtOAc. The isolated organic layers were washed with saturated NaHCO$_3$(aq), dried over MgSO$_4$, and concentrated in-vacuo. The crude product was purified over silica gel using 20%-40% EtOAc/hexanes, to provide a yield of 0.0683 g, 0.285 mmol, 48%. A sample of this material was successfully recrystallized using EtOH/H$_2$O and EtOAc/hexanes, individually.

While there have been described what are presently believed to be the preferred embodiments of the invention, those skilled in the art will realize that changes and modifications may be made thereto without departing from the spirit of the invention, and it is intended to include all such changes and modifications as fall within the true scope of the invention.

What is claimed is:

1. A method for preparing a compound having the formula III:

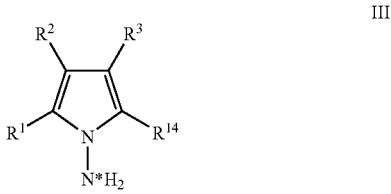

III wherein R$^1$ is, CN and CO$_2$R$^4$;
R$^2$ is C$_{1-4}$ alkyl;
R$^3$ is C$_{1-4}$ alkyl, and

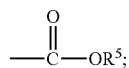

R$^4$ is C$_{1-4}$ alkyl, or aryl;
R$^5$ is C$_{1-4}$ alkyl; and
R$^{14}$ is selected from the consisting of hydrogen, cyano, alkyl or substituted alkyl, cycloalkyl or substituted cycloalkyl, heterocycle or substituted heterocycle, aryl or substituted aryl and C(=O)OR$_e$; and $R_e$ is alkyl or substituted alkyl, cycloalkyl or substituted cycloalkyl, heterocycle or substituted heterocycle, or aryl or substituted aryl;

comprising the steps of:
(a) cyclizing a compound of formula IIa or IIb:

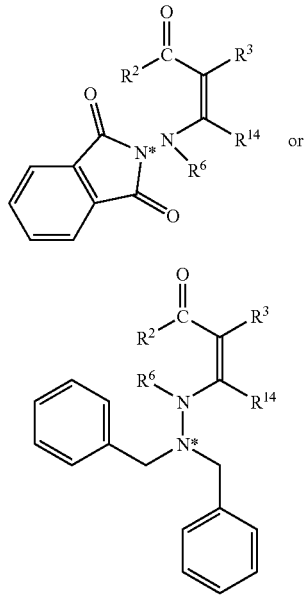

II(a)

II(b)

wherein $R^6$ is

—CH—$R^1$; and
  |
  $R^8$ $R^8$ is H or a halogen;
to form a compound of formula Ia or Ib:

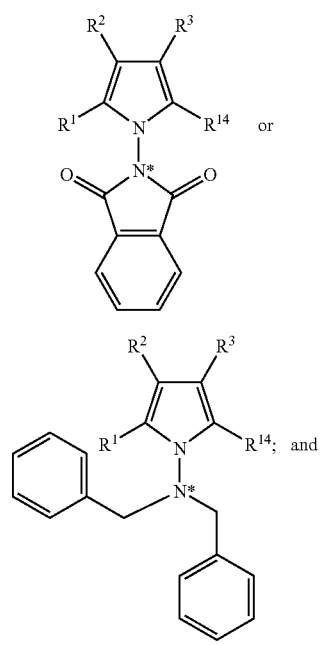

Ia

Ib (b) deprotecting the N* atom in the compound of formula Ia or Ib by reacting the compound of formula Ia or Ib with hydrazine or hydrogen to form a compound of formula III.

2. The method of claim 1, further including the step of forming a precursor of formula IIa or IIb, said precursor having the formula IVa or IVb,

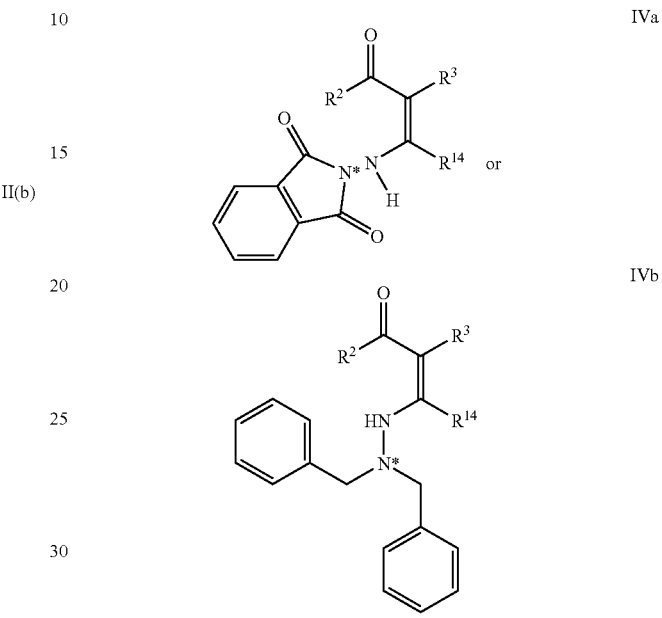

IVa

IVb wherein $R^2$ and $R^3$ are as defined in claim 1;
by reacting a hydrazine of the formula with a compound selected from the group consisting of VIIIa VIIIb wherein $R^{11}$ and $R^{12}$ are each independently $C_{1-4}$ alkyl.

3. The method of claim 2, wherein said compound of formula IIa or IIb is formed by reacting said compound of formula IVa or IVb with a reagent $XR^6$, wherein X is halogen and $R^6$ is as defined in claim 1.

4. The method of claim 1, wherein the compound of formula III is:

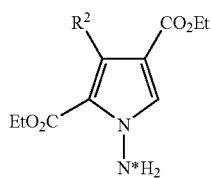

and $R^2$ is $C_{1-4}$ alkyl.

5. The method according to claim 1, wherein the compound of formula IIa or IIb is selected from the group consisting of

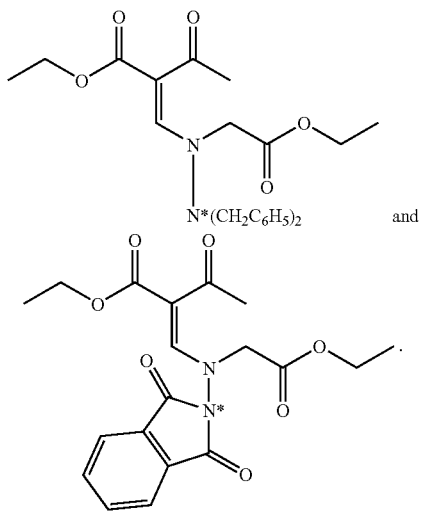

6. The method according to claim 1, wherein said cyclizing step is conducted in the presence of potassium-tert-pentylate.

7. The method according to claim 1, wherein said cyclizing step is conducted in the presence of 1,8-diazabicyclo[5.4.0] undec-7-ene and ethyl trifluoroacetate.

8. The method according to claim 1, wherein said cyclizing step comprises addition of dimethylformamide-dimethylacetal reagent followed by addition of acetic acid or trifluoroacetic anhydride.

9. The method of claim 2, wherein said compound of formula IIa or IIb is formed by reacting a compound of formula

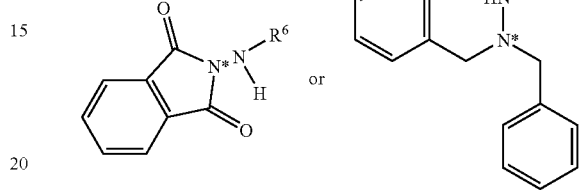

with a compound selected from the group consisting of:

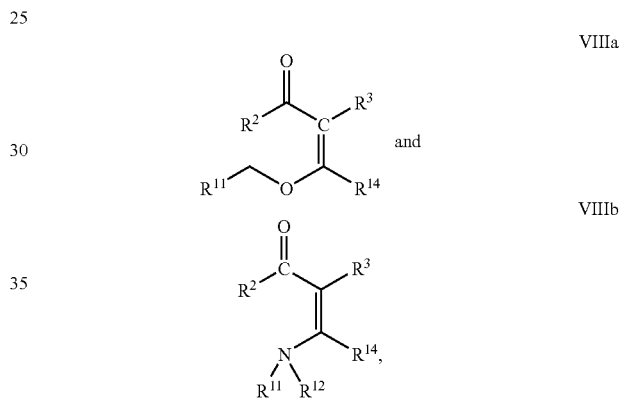

wherein $R^2$, $R^3$, $R^6$, and $R^{14}$ are as defined in claim 1 and $R^{11}$ and $R^{12}$ are as defined in claim 2.

* * * * *